(12) United States Patent
Fudemoto et al.

(10) Patent No.: US 7,935,184 B2
(45) Date of Patent: *May 3, 2011

(54) METHOD OF PREPARING IMIDAZOLIUM SURFACTANTS

(75) Inventors: Hiroyuki Fudemoto, Yokohama (JP); Xiaorong Wang, Hudson, OH (US); Victor J. Foltz, Akron, OH (US)

(73) Assignee: Bridgestone Corporation, Tokyo (JP)

( * ) Notice: Subject to any disclaimer, the term of this patent is extended or adjusted under 35 U.S.C. 154(b) by 646 days.

This patent is subject to a terminal disclaimer.

(21) Appl. No.: 11/455,615

(22) Filed: Jun. 19, 2006

(65) Prior Publication Data

US 2007/0293684 A1    Dec. 20, 2007

(51) Int. Cl.
    C09C 1/28    (2006.01)
    C07D 233/00  (2006.01)
    C08K 9/00    (2006.01)

(52) U.S. Cl. ........ 106/415; 523/216; 524/445; 524/447; 548/335.1

(58) Field of Classification Search .......... 524/186, 524/445, 447; 548/335.1; 106/415; 523/216
See application file for complete search history.

(56) References Cited

U.S. PATENT DOCUMENTS

| | | | |
|---|---|---|---|
| 2,493,318 A * | 1/1950 | Shonle et al. ............. 548/335.1 |
| 2,531,396 A | 11/1950 | Carter et al. |
| 3,972,963 A | 8/1976 | Schwab et al. |
| 4,233,409 A | 11/1980 | Bulkley |
| 4,247,434 A | 1/1981 | Lovelace et al. |
| 4,338,206 A | 7/1982 | Hammond et al. |
| 4,463,129 A | 7/1984 | Shinada et al. |
| 4,483,835 A * | 11/1984 | Zones .......................... 423/706 |
| 4,543,403 A | 9/1985 | Isayama et al. |
| 4,598,105 A | 7/1986 | Weber et al. |
| 4,602,052 A | 7/1986 | Weber et al. |
| 4,659,790 A | 4/1987 | Shimozato et al. |
| 4,665,963 A | 5/1987 | Timar |
| 4,764,572 A | 8/1988 | Bean, Jr. |
| 4,773,521 A | 9/1988 | Chen |
| 4,788,254 A | 11/1988 | Kawakubo et al. |
| 4,829,130 A | 5/1989 | Licchelli et al. |
| 4,829,135 A | 5/1989 | Gunesin et al. |
| 4,837,274 A | 6/1989 | Kawakubo et al. |
| 4,837,401 A | 6/1989 | Hirose et al. |
| 4,870,144 A | 9/1989 | Noda et al. |
| 4,871,814 A | 10/1989 | Gunesin et al. |
| 4,904,730 A | 2/1990 | Moore et al. |
| 4,904,732 A | 2/1990 | Iwahara et al. |
| 4,906,695 A | 3/1990 | Blizzard et al. |
| 4,920,160 A | 4/1990 | Chip et al. |
| 4,942,209 A | 7/1990 | Gunesin |
| 4,956,107 A | 9/1990 | Gutierrez et al. |
| 5,034,018 A | 7/1991 | Gutierrez et al. |
| 5,036,138 A | 7/1991 | Stamhuis et al. |
| 5,075,377 A | 12/1991 | Kawabuchi et al. |
| 5,100,947 A | 3/1992 | Puydak |
| 5,112,507 A | 5/1992 | Harrison |
| 5,120,379 A | 6/1992 | Noda et al. |
| 5,130,377 A | 7/1992 | Trepka et al. |
| 5,162,445 A | 11/1992 | Powers et al. |
| 5,169,914 A | 12/1992 | Kaszas et al. |
| 5,178,702 A | 1/1993 | Frerking, Jr. |
| 5,219,945 A | 6/1993 | Dicker et al. |
| 5,227,419 A | 7/1993 | Moczygemba et al. |
| 5,229,020 A | 7/1993 | Gutierrez et al. |
| 5,237,015 A | 8/1993 | Urban |
| 5,238,466 A | 8/1993 | Gutierrez et al. |
| 5,241,008 A | 8/1993 | Hall |
| 5,247,021 A | 9/1993 | Fujisawa et al. |
| 5,256,736 A | 10/1993 | Trepka et al. |
| 5,262,502 A | 11/1993 | Fujisawa et al. |
| 5,290,873 A | 3/1994 | Noda et al. |
| 5,290,875 A | 3/1994 | Moczygemba et al. |
| 5,290,878 A | 3/1994 | Yamamoto et al. |
| 5,308,364 A | 5/1994 | Gutierrez et al. |
| 5,331,035 A | 7/1994 | Hall |
| 5,336,712 A | 8/1994 | Austgen, Jr. et al. |
| 5,385,684 A | 1/1995 | Gutierrez et al. |
| 5,395,902 A | 3/1995 | Hall |
| 5,399,628 A | 3/1995 | Moczygemba et al. |
| 5,405,903 A | 4/1995 | Van Westrenen et al. |
| 5,421,866 A | 6/1995 | Stark-Kasley et al. |

(Continued)

FOREIGN PATENT DOCUMENTS

CN    1148060    4/1997

(Continued)

OTHER PUBLICATIONS

Baranova, O.V. et al., "Effect of the Structure of Phase-Transfer Catalyst on the Rate of Alkaline Hydrolysis of N-Benzyloxycarbonylglycine 4-Nitrophenyl Ester in the System Chloroform-Borate Buffer", Russian Journal of Organic Chemistry, vol. 38, No. 3, pp. 378-384, 2002.

Webb, Paul B. et al., "Continuous Flow Hydroformylation of Alkenes in Supercritical Fluid-Ionic Liquid Biphasic Systems", J. Am. Chem. Soc., vol. 125, pp. 15577-15588, 2003.

Wilkes, John S. et al., "Dialkylimidazolium Chloroaluminate Melts: A New Class of Room-Temperature Ionic Liquids for Electrochemistry, Spectroscopy, and Synthesis", Inorg. Chem., vol. 21, pp. 1263-1264, 1982.

International Search Report with Written Opinion dated Dec. 27, 2007 from corresponding PCT Application No. PCT/US2007/071539 (11 pp.).

Canham et al., "Formation of Worm-like Micelles from a Polystyrene-Polybutadiene-Polystyrene Block Copolymer in Ethyl Acetate", J.C.S. Faraday I, 76, 1857-1867 (1980).

(Continued)

Primary Examiner — Vickey Nerangis
(74) Attorney, Agent, or Firm — Meredith E. Hooker; Nathan T. Lewis

(57) ABSTRACT

The present invention provides a method for preparing an imidazolium surfactant using a mixing apparatus. The present invention also provides a nano-composite comprising a clay and the imidazolium surfactant, and a composition comprising a polymer and the nano-composite. The nano-composite is practically useful in formulating compositions such as rubber and tire products with improved and well-balanced properties including gas permeability, cure properties, and/or mechanical properties etc.

14 Claims, 1 Drawing Sheet

U.S. PATENT DOCUMENTS

| | | | |
|---|---|---|---|
| 5,436,298 A | 7/1995 | Moczygemba et al. | |
| 5,438,103 A | 8/1995 | DePorter et al. | |
| 5,447,990 A | 9/1995 | Noda et al. | |
| 5,462,994 A | 10/1995 | Lo et al. | |
| 5,476,521 A | 12/1995 | Gutierrez et al. | |
| 5,496,383 A | 3/1996 | Franz et al. | |
| 5,514,753 A | 5/1996 | Ozawa et al. | |
| 5,525,639 A | 6/1996 | Keneko et al. | |
| 5,527,870 A | 6/1996 | Maeda et al. | |
| 5,530,052 A * | 6/1996 | Takekoshi et al. | 524/447 |
| 5,567,845 A | 10/1996 | Franz et al. | |
| 5,576,372 A | 11/1996 | Kresge | |
| 5,576,373 A | 11/1996 | Kresge et al. | |
| 5,580,925 A | 12/1996 | Iwahara et al. | |
| 5,587,423 A | 12/1996 | Brandstetter et al. | |
| 5,594,072 A | 1/1997 | Handlin, Jr. et al. | |
| 5,614,579 A | 3/1997 | Roggeman et al. | |
| 5,627,252 A | 5/1997 | De La Croi Habimana | |
| 5,633,326 A | 5/1997 | Patil et al. | |
| 5,665,183 A | 9/1997 | Kresge | |
| 5,688,856 A | 11/1997 | Austgen, Jr. et al. | |
| 5,707,439 A | 1/1998 | Takekoshi et al. | |
| 5,728,791 A | 3/1998 | Tamai et al. | |
| 5,733,975 A | 3/1998 | Aoyama et al. | |
| 5,739,267 A | 4/1998 | Fujisawa et al. | |
| 5,763,551 A | 6/1998 | Wunsch et al. | |
| 5,773,521 A | 6/1998 | Hoxmeier et al. | |
| 5,777,037 A | 7/1998 | Yamanaka et al. | |
| 5,807,629 A | 9/1998 | Elspass | |
| 5,811,501 A | 9/1998 | Chiba et al. | |
| 5,834,563 A | 11/1998 | Kimura et al. | |
| 5,847,054 A | 12/1998 | McKee et al. | |
| 5,849,847 A | 12/1998 | Quirk | |
| 5,855,972 A | 1/1999 | Kaeding | |
| 5,856,513 A * | 1/1999 | Ue et al. | 548/347.1 |
| 5,883,173 A | 3/1999 | Elspass et al. | |
| 5,891,947 A | 4/1999 | Hall et al. | |
| 5,905,116 A | 5/1999 | Wang et al. | |
| 5,936,023 A | 8/1999 | Kato | |
| 5,955,537 A | 9/1999 | Steininger et al. | |
| 5,986,010 A | 11/1999 | Clites et al. | |
| 5,994,468 A | 11/1999 | Wang et al. | |
| 6,011,116 A | 1/2000 | Aoyama et al. | |
| 6,013,699 A | 1/2000 | Freeman | |
| 6,020,446 A | 2/2000 | Okamoto et al. | |
| 6,025,416 A | 2/2000 | Proebster et al. | |
| 6,025,445 A | 2/2000 | Chiba et al. | |
| 6,034,164 A | 3/2000 | Elspass | |
| 6,060,549 A | 5/2000 | Li et al. | |
| 6,060,559 A | 5/2000 | Feng et al. | |
| 6,087,016 A | 7/2000 | Feeney et al. | |
| 6,087,456 A | 7/2000 | Sakaguchi et al. | |
| 6,106,953 A | 8/2000 | Zimmermann et al. | |
| 6,117,932 A | 9/2000 | Hasegawa et al. | |
| 6,121,379 A | 9/2000 | Yamanaka et al. | |
| 6,147,151 A | 11/2000 | Fukumoto et al. | |
| 6,180,693 B1 | 1/2001 | Tang et al. | |
| 6,191,217 B1 | 2/2001 | Wang et al. | |
| 6,197,849 B1 * | 3/2001 | Zilg et al. | 523/216 |
| 6,204,354 B1 | 3/2001 | Wang et al. | |
| 6,225,394 B1 | 5/2001 | Lan et al. | |
| 6,255,372 B1 | 7/2001 | Lin et al. | |
| 6,268,451 B1 | 7/2001 | Faust et al. | |
| 6,277,304 B1 | 8/2001 | Wei et al. | |
| 6,348,546 B2 | 2/2002 | Hiiro et al. | |
| 6,359,075 B1 | 3/2002 | Wollum et al. | |
| 6,420,486 B1 | 7/2002 | DePorter et al. | |
| 6,437,050 B1 | 8/2002 | Krom et al. | |
| 6,472,460 B1 | 10/2002 | Okamoto | |
| 6,486,253 B1 | 11/2002 | Gilmer et al. | |
| 6,489,378 B1 | 12/2002 | Sosa et al. | |
| 6,573,330 B1 | 6/2003 | Fujikake et al. | |
| 6,598,645 B1 | 7/2003 | Larson | |
| 6,612,351 B1 | 9/2003 | Zanzig | |
| 6,617,020 B2 | 9/2003 | Zhou | |
| 6,649,702 B1 | 11/2003 | Rapoport et al. | |
| 6,689,469 B2 | 2/2004 | Wang et al. | |
| 6,706,804 B2 | 3/2004 | Resendes | |
| 6,706,813 B2 | 3/2004 | Chiba et al. | |
| 6,727,311 B2 * | 4/2004 | Ajbani et al. | 524/447 |
| 6,750,297 B2 | 6/2004 | Yeu et al. | |
| 6,759,464 B2 | 7/2004 | Ajbani et al. | |
| 6,777,500 B2 | 8/2004 | Lean et al. | |
| 6,780,937 B2 | 8/2004 | Castner | |
| 6,818,693 B2 | 11/2004 | Heinrich | |
| 6,835,781 B2 | 12/2004 | Kondou et al. | |
| 6,849,680 B2 | 2/2005 | Knudson, Jr. | |
| 6,852,229 B2 * | 2/2005 | Mehnert et al. | 210/634 |
| 6,858,665 B2 | 2/2005 | Larson | |
| 6,861,462 B2 | 3/2005 | Parker et al. | |
| 6,872,785 B2 | 3/2005 | Wang et al. | |
| 6,875,818 B2 | 4/2005 | Wang | |
| 6,908,958 B2 | 6/2005 | Maruyama | |
| 7,019,063 B2 | 3/2006 | Wada | |
| 7,241,829 B2 | 7/2007 | Chung et al. | |
| 7,371,793 B2 | 5/2008 | Gong et al. | |
| 7,388,033 B2 | 6/2008 | Nagy et al. | |
| 2002/0045714 A1 | 4/2002 | Tomalia et al. | |
| 2002/0095008 A1 | 7/2002 | Heinrich et al. | |
| 2002/0144401 A1 | 10/2002 | Nogueroles Vines et al. | |
| 2003/0004250 A1 | 1/2003 | Ajbani et al. | |
| 2003/0032710 A1 | 2/2003 | Larson | |
| 2003/0124353 A1 | 7/2003 | Wang et al. | |
| 2003/0130401 A1 | 7/2003 | Lin et al. | |
| 2003/0149185 A1 | 8/2003 | Wang et al. | |
| 2003/0198810 A1 | 10/2003 | Wang et al. | |
| 2003/0225190 A1 | 12/2003 | Borbely et al. | |
| 2004/0059057 A1 | 3/2004 | Swisher et al. | |
| 2004/0127603 A1 | 7/2004 | Lean et al. | |
| 2004/0143064 A1 | 7/2004 | Wang | |
| 2004/0147639 A1 | 7/2004 | Tsou | |
| 2004/0198917 A1 | 10/2004 | Castner | |
| 2004/0226643 A1 | 11/2004 | Yagi | |
| 2004/0249045 A1 | 12/2004 | Goodman | |
| 2005/0027057 A1 * | 2/2005 | Dias et al. | 524/445 |
| 2005/0027062 A1 | 2/2005 | Waddell | |
| 2005/0090611 A1 | 4/2005 | Huffer et al. | |
| 2005/0098252 A1 | 5/2005 | Muraoka | |
| 2005/0101743 A1 | 5/2005 | Stacy et al. | |
| 2005/0137288 A1 | 6/2005 | Maruo et al. | |
| 2005/0137310 A1 | 6/2005 | Gupta et al. | |
| 2005/0203248 A1 | 9/2005 | Zheng et al. | |
| 2005/0215693 A1 * | 9/2005 | Wang et al. | 524/445 |
| 2005/0222335 A1 | 10/2005 | Jones | |
| 2005/0277723 A1 | 12/2005 | Gong et al. | |
| 2006/0100339 A1 | 5/2006 | Gong et al. | |
| 2006/0173115 A1 | 8/2006 | Fudemoto et al. | |
| 2006/0205916 A1 * | 9/2006 | Takekoshi et al. | 528/272 |
| 2006/0235128 A1 | 10/2006 | Wang et al. | |
| 2007/0015853 A1 | 1/2007 | Weng et al. | |
| 2007/0129477 A1 | 6/2007 | Weng et al. | |
| 2007/0161734 A1 * | 7/2007 | Fudemoto et al. | 524/445 |
| 2007/0238822 A1 | 10/2007 | Wang et al. | |
| 2008/0009579 A1 | 1/2008 | Gong et al. | |
| 2008/0081866 A1 | 4/2008 | Gong et al. | |
| 2009/0182087 A1 | 7/2009 | Fudemoto et al. | |

FOREIGN PATENT DOCUMENTS

| | | |
|---|---|---|
| DE | 3434983 | 4/1986 |
| EP | 0143500 | 6/1985 |
| EP | 0265142 | 4/1988 |
| EP | 0590491 | 4/1994 |
| EP | 1099728 | 5/2001 |
| EP | 1125927 | 8/2001 |
| EP | 1134251 | 9/2001 |
| EP | 1273616 | 1/2003 |
| EP | 1321489 | 6/2003 |
| JP | 1279943 | 1/1989 |
| JP | 1955517 | 8/1989 |
| JP | 5132605 | 5/1993 |
| JP | 08199062 | 8/1996 |
| JP | 1125927 | 8/2001 |
| JP | 3356001 | 10/2002 |
| JP | 2003095640 | 4/2003 |
| WO | 9104992 | 7/1991 |
| WO | 9853000 | 11/1998 |
| WO | 9942518 | 8/1999 |

| | | |
|---|---|---|
| WO | 0187999 | 11/2000 |
| WO | WO0177081 | 10/2001 |
| WO | 0248257 | 6/2002 |
| WO | 0231002 | 7/2002 |
| WO | 02081233 | 10/2002 |
| WO | 02100935 | 12/2002 |
| WO | 02100936 | 12/2002 |
| WO | 03085040 | 10/2003 |
| WO | 2004/058874 | 7/2004 |
| WO | 2004/065430 | 8/2004 |
| WO | 2005/095506 | 10/2005 |
| WO | 2007/149842 | 12/2007 |

OTHER PUBLICATIONS

Chen, Wei et al., "Ultrahydrophobic and Ultrayophobic Surfaces: Some Comments and Examples", The ACS Journal of Surfaces and Colloids, vol. 15, No. 10, pp. 3395-3399 (May 11, 1999).

Cosgrove, T. et al., "Adsorbed Block Copolymer of Poly(2-vinylpyridine) and Polystyrene Studied by Neutron Reflectivity and Surface Force Techniques", Macromolecules, 26, pp. 4363-4367 (1993).

Coulson, S.R. et al., "Super-Repellent Composite Fluoropolymer Surfaces", The Journal of Physical Chemistry B, vol. 104, No. 37, pp. 8836-8840 (Sep. 21, 2000).

Dieterich, W. et al., "Non-Debye Relaxations in Disordered Ionic Solids", Chem. Chys., 284, pp. 439-467 (2002).

Ege, Seyhan, Organic Chemistry Structure and Reactivity, 3rd Edition, p. 959 (1994).

Greenwood, N.N. et al., Chemistry of the Elements, Pergaroen Press, New York, pp. 1126-1127 (1984).

Hardacre, C. et al., "Structure of molten 1,3-dimethylimidazolium chloride using neutron diffraction", J. Chem. Physics, 118(1), pp. 273-278 (2003).

Hoffman, B. et al., "Rheology of Nanocomposites Based on Layered Silicates and Polyamide-12", Colloid Polm. Sci.., 278, pp. 629-636 (2000).

Ishizu, Koji, "Star Polymers by Immobilizing Functional Block Copolymers", Star and Hyperbranched Polymers, ISBN 0-8247, pp. 135-178 (1999).

Jensen, M. et al., "EXAFS Investigations of the Mechanism of Facilitated Ion Transfer into a Room-Temperature Ionic Liquid", Jacs, 124, pp. 10664-10665 (2002).

Krishnamoorti, R. et al., "Rheology of End-Tethered Polymer Layered Silicate Nanocomposites", Macromol., 30, pp. 4097-4102 (1997).

Lagaly, Gehard, "Kink-Block and Gauche-Block Structures of Bimolecular Films", Chem. Int. Ed. Engl., vol. 15, No. 10, pp. 575-586 (1976).

Lawson, David F. et al., "Preparation and Characterization of Heterophase Blends of Polycaprolactam and Hydrogenated Polydienes", Central Research Journal of Applied Polymer Science, vol. 39, pp. 2331-2351 (1990).

Ma, Hongyang et al., "Reverse Atom Transfer Radical Polymerization of Methyl Methacrylate in Room-Temperature Inoic Liqquids", J. Polym. Sci., A. Polym. Chem., 41, pp. 143-151 (2003).

Ma, Yuhong et al., "Synthesis and Properties of the Ionomer Diblock Copolymer Poly(4-vinylbenzyl triethyl ammonium bromide)-b-Polyisobutene", Journal of Polymer Science: Part A: Chemistry, vol. 41, pp. 2755-2764 (2003).

Mandema et al., "Association of Block Copolymers in Selective Solvents, 1 Measurements on Hydrogenated Poly(styrene-isoprene) in Decane and in trans-Decalin", Makromol. Chem. 180, pp. 1521-1538 (1979).

Mendizabal, E. et al., "Functionalized Core-Shell Polymers Prepared by Microemulsion Polymerization", ANTEC 1997 Plastics: Plastics Saving Planet Earth, vol. 2: Materials Conference Proceedings, pp. 1733-1737.

Moller, Martin et al., "Mineralization of Gold in Block Copolymer Micelles", Macromol. Symp., 117, pp. 207-218 (1997).

Mossmer, Stefan et al., "Solution Behavior of Poly(styrene)-block-poly(2-vinylpyridine) Micelles Containing Gold Nanoparticles", Macromolecules, 33, pp. 4791-4798 (2000).

Quirk, Roderic P. et al., "Controlled Anionic Synthesis of Polyisoprene-Poly(2-vinylpyridine) Diblock Copolymers in Hydrocarbon Solution", Macromolecules, 34, pp. 1192-1197 (2001).

Ren, J., "Linear Viscoelasticity of Disordered Polystyrene-Polyisoprene . . . Layered-Silicate Nanocomposites", Macromol., pp. 3739-3746 (2000).

Tiyapiboonchaiya, C. et la., "Polymer-in-Ionic-Liquid Electrolytes", Micromol. Chem. Phys., 203, pp. 1906-1911 (2002).

Tomalia, Donald A. et al., "Dendritic Macromolecules: Synthesis of Starburst Dendrimers", Macromolecules vol. 19, No. 9, pp. 2466-2468 (1986).

Tuzar et al., "Anomalous Behaviour of Solutions of Styrene-Butadiene Block Copolymers in Some Solvents", Makromol. Chem. 178, 22743-2746 (1977).

Utiyama et al., "Light-Scattering Studies of a Polystyrene-Poly(methyl methacrylate) Two-Blcok Copolymer in Mixed Solvents", Macromolecules, vol. 7, No. 4, (Jul.-Aug. 1974).

"Quaternary Ammonium Compounds", Encyclopedia of Chem Tech., 4th Ed., vol. 20, pp. 739-767 (1996).

Gilman, J.W. et al., "Recent Advances in Flame Retardant Polymer Nanocomposites", pp. 273-283.

Hay, J.N. et al., "A Review of Nanocomposites" [2000].

Wang, Yizhong et al., "Preparation and Characterization of Rubber-Clay Nanocomposites", Journal of Applied Polymer Science, vol. 78, pp. 1879-1883 (2000).

* cited by examiner

METHOD OF PREPARING IMIDAZOLIUM SURFACTANTS

BACKGROUND OF THE INVENTION

The present invention is directed to a method of preparing imidazolium surfactant. The present invention is also directed to a nano-composite comprising the imidazolium surfactant and a clay, and a composition comprising the nano-composite and a polymer. The composition is useful in preparing rubber products with well-balanced gas impermeability, cure properties, and mechanical properties etc.

In manufacturing a satisfactory rubber product, one needs to consider a wide range of factors and various balances between them, such as gas permeability, curing properties such as curing time and curing capability, traction characteristics on dry or wet surface, rolling resistance, tread-wear resistance, ring tensile, vulcanization plateau, Shore A hardness, rubber damping properties, elongation, strain, specific gravity, reliability, manufacturability, and cost effectiveness, among others. For example, gas impermeability is important for many products such as butyl rubber, because unsaturated bonds in butyl rubber can be attacked by atmospheric ozone. These attacks may, over time, lead to oxidative degradation, which may subsequently lead to chain cleavage. As such, there exists a continuous interest in lowering gas permeability of polymers.

Since the discovery of exfoliated nylon/clay nano-composites by Usuki et al. (*J. Mater. Res.* 1993, 8, 1174), people have made extensive efforts to lower gas permeability by using well-exfoliated layered materials. A common morphology for miscible polymer-layered material dispersions is known as intercalation and exfoliation, which improves polymeric mechanical, gas barrier/permeability, thermal, and heat distortion temperature properties. However, for polymers, particularly nonpolar polymers, well-exfoliated polymer-layered material nano-composites are notoriously difficult to obtain. For example, Wang et. al in the Journal of *Applied Polymer Science*, Vol. 78, 1879-1883 (2000) describe a process of making clay-rubber mixtures by mixing a styrene-vinylpyridine-butadiene latex with a hydrophilic unmodified clay. The expansion of the clay gallery was reported to only increase from 1.24 to 1.46 nm. This limited extent of intercalation is not expected to provide substantial property enhancement.

Although organic ammonium salts have shown improved clay exfoliation, they typically have a low decomposition temperature. Accordingly, these materials cannot be extruded at high temperature as may be required with a resin such as nylon, PP, PET, etc. Furthermore, organo-clays treated by the ammonium salts may damage or retard the cure process of the rubbery material, especially when free radical sulfur, or ZnO cure are employed.

Advantageously, the present invention provides a method of preparing an imidazolium surfactant that may have a high decomposition temperature. The imidazolium surfactant may be used to prepare nano-composites such as organo-clays and products including the nano-composites.

SUMMARY OF THE INVENTION

According to one embodiment, the present invention provides a method of preparing imidazolium surfactants in the substantial absence of a solvent. As used herein, substantial absence of a solvent means less than 20% by weight solvent relative to the reactants, more preferably, less than 10% by weight solvent, and most preferably, less than 1% by weight.

A second aspect provides a nano-composite comprising a clay and an imidazolium surfactant, wherein the clay is exfoliated or intercalated by the imidazolium surfactant.

A third aspect provides a composition comprising the nano-composite and a polymer, wherein the clay of the nano-composite is exfoliated or intercalated by the imidazolium surfactant or by a mixture of the imidazolium surfactant and the polymer.

A fourth aspect of the invention provides an article such as a tire including the nano-composite.

Other aspects of the invention may be appreciated from the following detailed description.

BRIEF DESCRIPTION OF THE DRAWINGS

The invention may take form in various components and arrangements of components, and in various steps and arrangements of steps. The drawings, wherein like reference numerals denote like components throughout the several views, are only for purposes of illustrating preferred embodiments and are not to be construed as limiting the invention.

In the drawings appended hereto.

DETAILED DESCRIPTION OF ILLUSTRATIVE EMBODIMENTS

Figure 1:
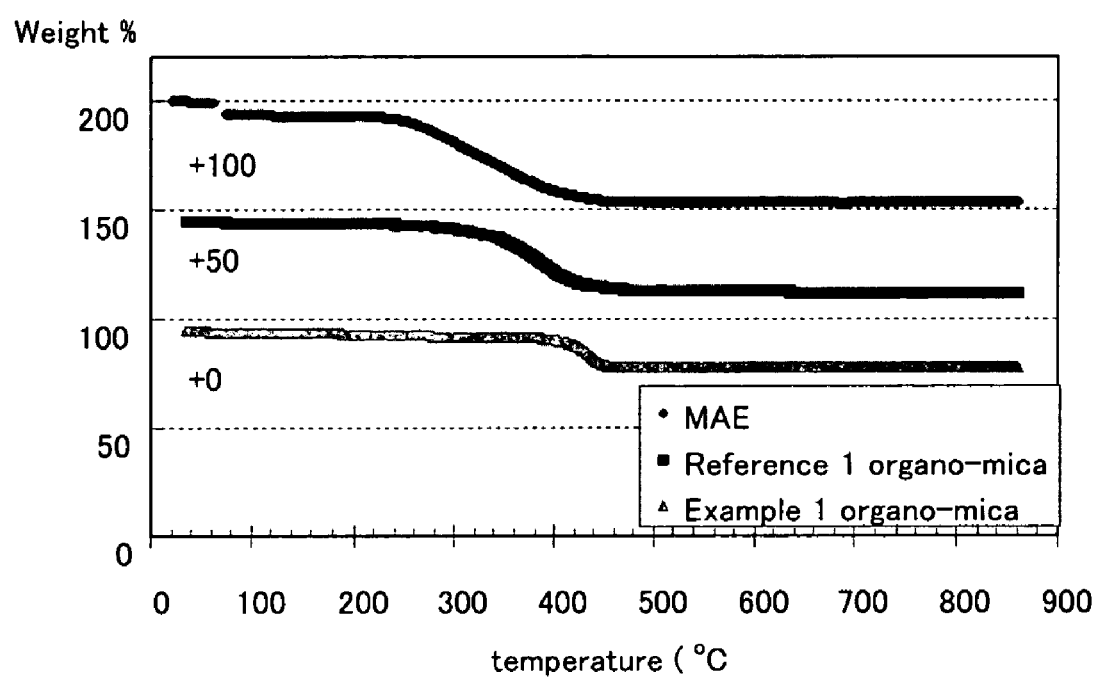
FIG. 1 shows the TGA analysis results for organo-clays in an exemplary embodiment of the invention.

It is to be understood herein, that if a "range" or "group" is mentioned with respect to a particular characteristic of the present invention, for example, ratio, percentage, chemical group, and temperature etc., it relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-range or sub-group encompassed therein; and similarly with respect to any sub-ranges or sub-groups therein.

In one of its embodiments, the present invention provides a method of preparing an imidazolium surfactant, which comprises the steps of (i) providing two or more reactants, (ii) mixing the reactants, and (iii) collecting the target imidazolium surfactant.

In general, any reactants that yield the target imidazolium surfactant may be used as the starting materials. The starting reactants may be selected from halogenated $C_{\geq 3}$ hydrocarbons and imidazole derivatives. The symbol $C_{\geq 3}$ denotes "containing no less than 3 carbon atoms". For example, the halogenated $C_{\geq 3}$ hydrocarbon of the present invention may include any saturated or unsaturated, substituted or unsubstituted, straight or branched, cyclic or acyclic $C_3$-$C_{50}$ alkyl or arylalkyl halide. Examples of halogenated $C_{\geq 3}$ hydrocarbons include, but are not limited to, benzyl chloride, n-dodecyl or lauryl halide, n-tridecyl halide, n-tetradecyl halide, myristyl halide, n-pentadecyl halide, n-hexadecyl or cetyl halide, palmityl halide, n-heptadecyl halide, n-octadecyl halide, octyl chloride, hexadecyl chloride, 1-cinnamyl chloride, 6-chloro-1-hexene, 1-bromodocosane, 1-chlorobutane, and the like. Examples of imidazole derivatives include, but are not limited to, imidazole, 1-methylimidazole, 1,2-dimethylimidazole, 1-ethylimidazole, 1-ethyl-2-methyl-imidazole, 1,2-diethylimidazole, 1-benzylimidazole, 1-benzyl-2-methylimidazole, 1-benzyl-2-ethylimidazole, 1-dodecyl-imidazole, 1-dodecyl-2-methyl-imidazole, 1-dodecyl-2-ethyl-imidazole, and the like. Advantageously, several of these imidazole derivatives are environmentally friendly green solvents.

In a specific example, the starting material comprises a halogenated $C_{\geq 3}$ hydrocarbon such as benzyl chloride and an imidazole derivative such as 1-benzyl-2-methylimidazole, and the targeted synthesis route is illustrated as the following.

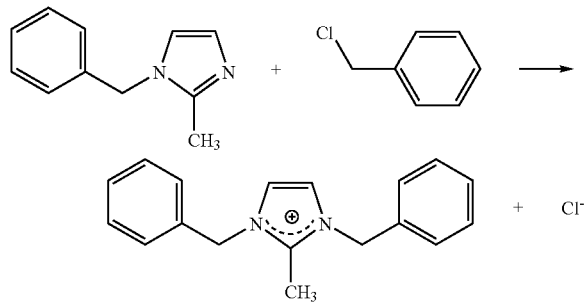

Depending upon the chemical and physical properties of the selected reactants (such as melting point), the mixing apparatus may be selected from those known to a skilled person in the art that are able to obtain a homogeneous mixture of the two or more reactants. Exemplary mixing apparatuses include, but are not limited to, a Brabender mixer or a Brabender plastograph, a two-stem mixer, a twin-screw extruder, a single-screw extruder, a plastomill or a rubber mill, a Banbury mixer, a Buss-Ko kneader, a Farrel continuous mixer, a Henschel mixer, a ribbon blender, a V-type blender, a mixing roll, a kneader, a static mixer, an impingement mixer, and the like.

The mixing apparatus may be configured and equipped that it has one or more further functions selected from the group consisting of temperature control, torque control, start-stop controls, rotation speed control, reactor environment control, reactants feeding measurement and control, and the like, and any combination thereof. For example, the mixing apparatus may be equipped with a temperature control console which includes temperature sensors, cooling means and temperature indicators etc.; the mixing apparatus may also be equipped with a drive motor having variable speed and constant torque control, start-stop controls and ammeter. Also, the mixing apparatus may be equipped with a reactor environment control system that introduces an inert gas such as nitrogen to protect reactions occurring in the apparatus.

The mixing reaction may last until the desired product is generated with desired yield and purity. In a variety of exemplary embodiments, the period of mixing and reaction time may be from about 5 minutes to about 2,000 minutes preferably from about 30 minutes to about 1,500 minutes, more preferably from about 60 minutes to about 1,000 minutes. According to one example, the reaction between benzyl chloride and 1-benzyl-2-methylimidazole may last about 15 minutes to 90 minutes.

Other reaction parameters may be determined depending upon the target imidazolium surfactant. In general, the mixing and reaction may be conducted at a temperature of from about 30° C. to about 300° C., from about 50° C. to about 250° C., of from about 70° C. to about 200° C. According to one example, the reaction between benzyl chloride and 1-benzyl-2-methylimidazole may be conducted at a temperature of from about 23° C. to about 250° C. The rotation speed of a mixing apparatus may be controlled at a value of from about 10 rpm to about 200 rpm, from about 20 rpm to about 150 rpm, or from about 30 rpm to about 100 rpm. According to one example, the rotation speed for benzyl chloride and 1-benzyl-2-methylimidazole may be controlled at a value of from about 10 rpm to about 100 rpm.

In an exemplary method of preparing an imidazolium surfactant, a twin-screw extruder, a Brabender, or a two-stem mixer can be used as the mixing apparatus. Representative versions of these devices are available commercially. Before the yielded imidazolium surfactant is dried, it may be optionally washed with a solvent such as hexane, toluene, and the like, one or more times.

Various imidazolium surfactants may be produced, however, it should be understood that an imidazolium surfactant typically contains a positively charged imidazolium moiety and a negatively charged counter ion(s). For simplicity, the counter ion may not be so explicitly stated when the surfactant is described. Exemplary counter ions of the imidazolium surfactant may include, but are not limited to, simple anions such as $Cl^-$, $Br^-$, $F^-$, $I^-$, $O^{2-}$, $S^{2-}$, $Se^{2-}$, $Te^{2-}$, $N^{3-}$, $As^{3-}$, and the like; and polyatomic anions such as $BF_4^-$, $PF_6^-$, $CO_3^{2-}$, $HCO_3^-$, $SO_4^{2-}$, $CF_3SO_3^-$, $SO_3^{2-}$, $S_2O_3^{2-}$, $HSO_4^-$, $H_2PO_4^-$, $HPO_4^{2-}$, $PO_4^{3-}$, $NO_2^-$, $NO_3^-$, $C_2O_4^{2-}$, $C_2H_3O_2^-$, $OH^-$, $O_2^{2-}$, $N_3^-$, $CrO_4^{2-}$, $Cr_2O_7^{2-}$, $BO_3^{3-}$, $MnO_4^-$, $AsO_4^{3-}$, $SCN^-$, $CN^-$, $CNO^-$, $ClO^-$, $ClO_2^-$, $ClO_3^-$, $ClO_4^-$, $BrO^-$, $BrO_2^-$, $BrO_3^-$, $BrO_4^-$, $IO^-$, $IO_2^-$, $IO_3^-$, $IO_4^-$, and the like. In one exemplary embodiment, the counter ion is $Cl^-$ or $Br^-$.

The imidazolium surfactant may have a general formula (I) as shown below:

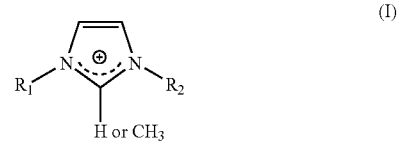

(I)

wherein at least one of $R_1$ and $R_2$ group is any of the $C_{\geq 3}$ hydrocarbon group.

Exemplary $C_{\geq 3}$ hydrocarbon groups of the invention include, but are not limited to, benzyl, 2-phenylethyl, 3-phenyl-3-ene-propyl, 6-ene-hexyl, butyl, isobutyl, behenyl, palmitoleyl, oleyl, linoleyl, linelenyl, erucyl, capryl, tallow, n-pentyl, any isopentyl, n-hexyl, any isohexyl, n-heptyl, any isoheptyl, n-octyl, any isooctyl, n-nonyl, any isononyl, n-decyl, any isodecyl, n-undecyl, any isoundecyl, n-dodecyl or lauryl, any isododecyl, n-tridecyl, any isotridecyl, n-tetradecyl, myristyl, any isotetradecyl, n-pentadecyl, any isopentadecyl, n-hexadecyl or cetyl, palmityl, any isohexadecyl, n-heptadecyl, any isoheptadecyl, n-octadecyl, stearyl, any isooctadecyl, n-nonadecyl, any isononadecyl, n-eicosyl, any isoeicosyl, n-henicosyl, any isohenicosyl, n-docosyl, any isodocosyl, n-tricosyl, any isotricosyl, n-tetracosyl, any isotetracosyl, n-pentacosyl, any isopentacosyl, n-hexacosyl, any isohexacosyl, n-heptacosyl, any isoheptacosyl, n-octacosyl, any isooctacosyl, n-nonacosyl, any isononacosyl, n-triacontyl, any isotriacontyl, n-hentriacontyl, any isohentriacontyl, n-dotriacontyl, any isodotriacontyl, n-tritriacontyl, any isotritriacontyl, n-tetratriacontyl, any isotetratriacontyl, n-pentatriacontyl, any isopentatriacontyl, n-hexatriacontyl, any isohexatriacontyl, n-heptatriacontyl, any isoheptatriacontyl, n-octatriacontyl, any isooctatriacontyl, n-nonatriacontyl, any isononatriacontyl, n-tetracontyl, any isotetracontyl, n-hentetracontyl, any isohentetracontyl, n-dotetracontyl, any isodotetracontyl, n-tritetracontyl, any isotritetracontyl, n-tetratetracontyl, any isotetratetracontyl, n-pentatetracontyl, any isopentatetracontyl, n-hexatetracontyl, any isohexatetracontyl, n-heptatetracontyl, any isoheptatetracontyl, n-octatetracontyl, any isooctatetracontyl, n-nonatetracontyl, any isononatetracontyl, n-pentacontyl, isopentacontyl and mixtures thereof.

The C≧3 hydrocarbon group can more specifically be selected from the group consisting of n-dodecyl or lauryl, n-tridecyl, n-tetradecyl, myristyl, n-pentadecyl, n-hexadecyl or cetyl, palmityl, n-heptadecyl, n-octadecyl, and the mixture thereof.

The imidazolium surfactant comprising the following formula (I') compound, may be particularly effective in improving the gas barrier property of a polymeric nano-composite product.

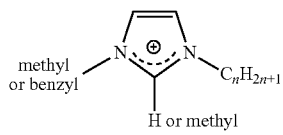
(I')

wherein n=12, 13, 14, 15, 16, 17 or 18.

The several exemplary imidazolium surfactants include one or more of the following:

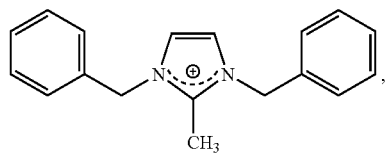
(I-1)

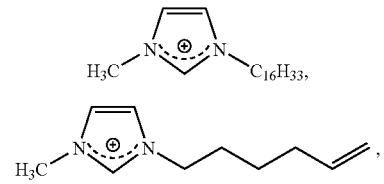
(I-2)

(I-3)

(I-4)

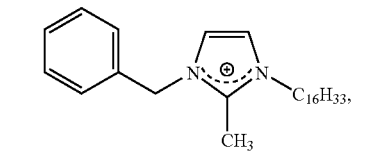
(I-5)

(I-6)

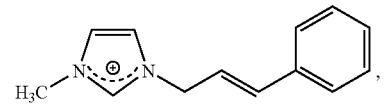
(I-7)

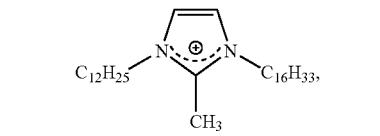
(I-8)

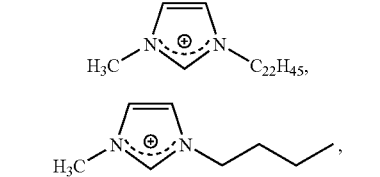

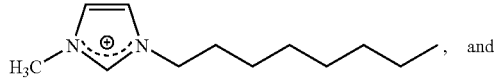
(I-9)

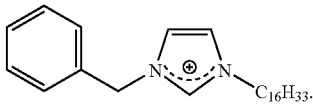
(I-10)

The method of the invention can even without the optional washing steps, produce targeted imidazolium surfactants with higher purity, e.g. NMR purity, and more accurate melting point than conventional manual methods. Moreover, the method provides an easy and cost-effective way of synthesis, and therefore improves the manufacturability of imidazolium surfactants.

The imidazolium surfactant as described supra, can be used in the exfoliation or intercalation as described in WO9853000; JP08199062; JP Publication Number 2003-95640A; U.S. Pat. Nos. 6,197,849; 5,707,439; J. S. Wikes, J. A. Levisky, B. A. Wilson, *Inorg. Chem.* 1982, 21, 1263-1264; J N Hay and S J Shaw "A Review of Nanocomposites 2000"; and Gilman, J. W. et al "Recent Advances in Flame Retardant Polymer Nanocomposites", herein incorporated by reference.

The imidazolium surfactant may work alone or, optionally, in combination with one or more conventional surfactants, in exfoliating clay and forming the nano-composite. Some representative examples of conventional surfactants include methyl tallow bis-2-hydroxyethyl ammonium salt, dimethyl hydrogenated-tallow (2-ethylhexyl) ammonium salt, dimethyl benzyl hydrogenated-tallow ammonium salt, dimethyl dihydrogenated tallow ammonium salt, N-tallow alkyltrimethylenediamine, hydrogenated tallow amine, octadecylamine, octadecylamine and γ-aminopropyltriethoxy silane, polyoxyethylene decycloxypropylamine, n-dodecylpyrrolidone, or their combinations and analogs.

Examples of conventional surfactants include quarternary ammonium surfactants, such as dimethyl ditallow ammonium, trimethyl tallow ammonium, dimethyl dihydrogenated tallow ammonium, methyl ethyl ditallow ammonium, methyl ethyl benzyl tallow ammonium, dimethyl ethyl tallow ammonium, and the like. For example, dimethyl ditallow ammonium may be used first to treat mica, before the imidazolium surfactant of the invention is used.

The imidazolium surfactants can be used to exfoliate a layered material and form useful products such as a nano-composite, or organo-clay, or exfoliated clay, or intercalated clay (terms used interchangeably herein). "Layered material" means an inorganic material that is in the form of a plurality of adjacent bound layers or plates. In typical embodiments, layered materials of the invention are those that can give at least one of the imidazolium surfactants access to their interlayer spaces through exchanging, partially or completely, cations with the imidazolium surfactants, a process called intercalation.

In many cases, the layered material is clay, which typically comprises an inorganic phase having layered materials in plates or other shapes with a significantly high aspect ratio. The aspect ratio is defined as the ratio of the largest and smallest dimension of the clay particles.

Exemplary clays include, but are not limited to, mica; synthetic mica; smectites such as montmorillonite (Bentonite), sodium montmorillonite, magnesium montmorillonite, calcium montmorillonite, beidellite, nontronite, hectorite, sodium hectorite, saponite, synthetic saponite, and sauconite; pyrophyllite; glauconites; vermiculites; polygorskines; sepiolites; allophanes; imogolites; talc; fluoro-mica; illites; glauconite; phyllosilicates; volkonskoite; sobockite; stevensite; svinfordite; magadiite; kenyaite; kaolinite; dickite; nacrite; anauxite; ledikite; montronite; silicate; halloysite; metahalloysite; sericite; allophone; serpentine clays; chrysotile; antigorite; attapulgite; sepiolite; palygorskite; Kibushi clay; gairome clay; hisingerite; chlorite; and the like; and mixtures thereof.

In exemplary embodiments, clays such as mica or synthesized mica may be untreated, or may have been chemically pretreated to make them more compatible with organic materials, as well as the imidazolium surfactants of the invention. For example, a layered silicate clay may be modified with up to about 70 parts by weight of a quaternary ammonium salt surfactant selected from the group consisting of methyl tallow bis-2-hydroxyethyl ammonium halides, methyl tallow bis-2-hydroxyethyl ammonium alkyl sulfates, methyl tallow bis-2-hydroxyethyl ammonium nitrate, methyl tallow bis-2-hydroxyethyl ammonium hydroxide, methyl tallow bis-2-hydroxyethyl ammonium acetate, methyl tallow bis-2-hydroxyethyl ammonium phosphate, dimethyl hydrogenated-tallow (2-ethylhexyl) ammonium halides, dimethyl hydrogenated-tallow (2-ethylhexyl) ammonium alkyl sulfates, dimethyl hydrogenated-tallow (2-ethylhexyl) ammonium nitrate, dimethyl hydrogenated-tallow (2-ethylhexyl) ammonium hydroxide, dimethyl hydrogenated-tallow (2-ethylhexyl) ammonium acetate, dimethyl hydrogenated-tallow (2-ethylhexyl) ammonium phosphate, dimethyl dehydrogenated-tallow ammonium halides, dimethyl dehydrogenated-tallow ammonium alkyl sulfates, dimethyl dehydrogenated-tallow ammonium nitrate, dimethyl dehydrogenated-tallow ammonium hydroxide, dimethyl dehydrogenated-tallow ammonium acetate, and dimethyl dehydrogenated-tallow ammonium phosphate, among others.

In specific embodiments, mica from Coop Chemical Co. with a trade name ME100 is used as the clay in preparing nano-composites.

In a variety of exemplary embodiments, the weight ratio between the clay and the imidazolium surfactant can be from about 20:80 to about 80:20, from about 30:70 to about 70:30, or preferably from about 40:60 to about 60:40.

Accordingly, the invention provides a method for preparing nano-composites. The nano-composite comprises a clay and a imidazolium surfactant as described supra. The clay is exfoliated or intercalated by the imidazolium surfactant. In various embodiments, the method comprises blending a sufficient amount of the imidazolium surfactant into the clay, as described for example in U.S. Pat. Nos. 2,531,427, 2,531,440, 5,110,501, and 5,334,241, each of which is herein incorporated by reference.

Typical clays have a layered lamellar structure with a gap of about 0.1 nm between each layer and exchangeable cationic species such as $K^+$, $Na^+$ or $Ca^{2+}$ on the surface of each layer and between clay galleries or layers. The cationic species are attached by an ionic interaction with the negatively charged surface of the clay layers, and create a net neutral charge between clay layers.

To exfoliate or intercalate a clay, its lamellar structure must be opened to some degree in order to permit the cation exchange reaction to take place with the imidazolium surfactant of the invention. In a variety of embodiments, at least a portion of these exchangeable cationic species are substituted by the imidazolium surfactant of the invention.

Any suitable clay exfoliation technique may be used to prepare the nano-composites of the invention. Exemplary clay-exfoliation techniques include, but are not limited to, direct addition method, and slurry method, among others.

In a slurry method, clay may be first swelled by placing it in water. Swelling takes place because the cations of the clay become solubilized in the water, and salvation relaxes the clay's structure in order to permit penetration of imidazolium surfactants and cation exchange thereafter. Adjacent clay layers are believed to be repulsed by their similar negative charges, resulting in gaps between them. An imidazolium surfactant may then be added to the swollen clay to form an organo-clay or nano-composite. Alternatively, before addition of the imidazolium surfactant, the clay may be pre-exfoliated with a cationic surfactant such as an ammonium salt. In some embodiments, if the imidazolium surfactant used is an ionic liquid, the clay may be directly mixed with the imidazolium surfactant. The imidazolium surfactant is attracted to the negatively charged surface of the clay, keeping the swelling state stable. Preferably, the exfoliated clay will have an average between-layer gap greater than about 0.1 nm, preferably greater than 1.0 nm, and more preferably greater than about 3.0 nm, such as about 5-10 nm. A dewatering step may be performed to dry the exfoliated clay. Optionally, the dried exfoliated clay is washed with an alcohol, such as, but not limited to, isopropanol, propanol, butanol, hexanol, and the like, and the mixture thereof.

The present invention also provides a composition comprising (i) a clay, (ii) an imidazolium surfactant, and (iii) a polymer, wherein the clay is exfoliated or intercalated by the imidazolium surfactant or by a mixture of the imidazolium surfactant and the polymer.

When a polymer is incorporated into the nano-composites as described supra, because of the presence of the imidazolium surfactant, a relatively homologous morphology can be formed. The polymer may penetrate between the clay layers and further separate the layers of the clay, based on the possibility that the added polymer and the imidazolium surfactant can attract each other at, e.g., their hydrophobic portions. Preferably, the large molecule size of the imidazolium surfactant and/or the added polymer may counteract any remaining Van der Waals interactions between the clay layers and the clay can be fully or almost fully exfoliated, i.e. separated into discrete layers.

Based on the total weight of the composition, the amount of the nano-composite (clay+imidazolium surfactant) may be from about 0.1% (wt) to about 90% (wt), preferably from about 1% (wt) to about 50% (wt), and more preferably from about 1% (wt) to about 30% (wt).

Based on the total weight of the composition, the amount of the polymer may be from about 99.9% (wt) to about 10% (wt), preferably from about 99% (wt) to about 50% (wt), and more preferably from about 99% (wt) to about 70% (wt).

Before the nano-composite (clay+imidazolium surfactant) is added to the polymer in forming the composition, at least about 50% (wt) of the clay, preferably at least about 70% (wt) of the clay, and more preferably at least about 90% (wt) of the clay, is exfoliated. After the nano-composite is blended with the polymer in forming the composition, at least about 50% (wt) of the clay, preferably at least about 70% (wt) of the clay, and more preferably at least about 90% (wt) of the clay, is exfoliated.

Before the nano-composite is blended with the polymer in forming the composition, the exfoliated clay may have an average between-layer gap greater than about 3 nm, preferably greater than 5 nm, and more preferably greater than about 10 nm. After the nano-composite is blended with the polymer in forming the composition, the exfoliated clays may have an average between-layer gap greater than about 3 nm, preferably greater than 7 nm, and more preferably greater than about 15 nm.

There is no specific limitation on the polymer to be used with the nano-composites. Preferred polymers are those that can intercalate between clay layers more effectively with than without the aid of the imidazolium surfactant as demonstrated above. The polymer can have a saturated or unsaturated polyvinyl-type (i.e., carbon-chain) backbone, such as polychloroprene, polyethylene, isobutene-isoprene rubber (butyl rubber, IIR), halogenated butyl rubber (HIIR) such as CIIR and BrIIR, neoprene rubber, nitrile rubber (NBR), 1,2-polybutadiene, polyallene, polybutadiene (butadiene rubber, BR), polyisobutylene (PIB), polyisoprene, 3,4-polyisoprene, poly(methyl acrylate), poly(methyl vinyl ketone), ethylene-propylene elastomer, polystyrene (PS), polyacrylamide, poly(acrylamide oxime), polypropylene (PP), styrene-butadiene rubber (SBR), poly(methyl methacrylate), acrylonitrile-butadiene-styrene terpolymer (ABS), poly(vinyl chloride) (PVC), poly(vinylidene chloride), poly(vinyl pyridine), poly(vinyl pyrrolidone), poly(acrylic anhydride), polyacrylonitrile, styrene-acrylonitrile copolymer (SAN), ethylene-vinyl acetate copolymer (EVA), and the like. Of course, the polymer in the composition can possess a backbone with one or more functional groups such as carbonyl, or a non-carbon element such as N, S or O etc. (i.e. heterochain polymer). Exemplary heterochain polymers include, but are not limited to, polyether such as poly(oxyethylene), polyformadehyde, poly(phenylene oxide) or polyacetaldehyde; polyacrolein, polysulfide, polysulfone, poly(alkylene polysulfide), polyester, polycarbonate, polyphosphate ester, polyamide, polyurea, polyurethane, heterocyclic polymer, polyhydrazides, polyimide, melamine-formaldehyde resin (MF), polysaccharides, phenol-formaldehyde resin (PF), and polyanhydride etc. The polymer can also be an inorganic or inorganic/organic polymer such as polysiloxane, polysilane, carborane polymer, and organometallic polymer etc.

The composition may be used to manufacture rubber articles such as tires. The rubber material may be made by polymerization or copolymerization of a wide range of monomers, which include, but are not limited to, conjugated dienes such isoprene, butadiene, and the like; alkyl acrylates such as methyl acrylate, ethyl acrylate, butyl acrylate, methyl methacrylate, and the like; vinylidene monomers having one or more terminal vinyl groups; vinyl aromatics such as styrene, α-methylstyrene, t-butylstyrene, bromostyrene, chlorostyrene, fluorostyrene, and the like; α-olefins such as ethylene, propylene, 1-butene, and the like; vinyl halides, such as vinylbromide, chloroethane (vinylchloride), vinylfluoride, vinyliodide, 1,2-dibromoethene, 1,1-dichloroethene (vinylidene chloride), 1,2-dichloroethene, and the like; vinyl esters such as vinyl acetate; α,β-olefinically unsaturated nitriles, such as acrylonitrile and methacrylonitrile; α,β-olefinically unsaturated amides, such as acrylamide, N-methyl acrylamide, N,N-dimethylacrylamide, methacrylamide, and the like.

In some embodiments, vinyl aromatic monomers are incorporated into polydiene rubbers. Such vinyl aromatic monomers are selected so as to be copolymerizable with the conjugated diolefin monomers being utilized. Generally, any vinyl aromatic monomer which is known to polymerize with organolithium initiators can be used. Such vinyl aromatic monomers typically contain from 8 to 20 carbon atoms. Usually, the vinyl aromatic monomer will contain from 8 to 14 carbon atoms. The most widely used vinyl aromatic monomer is styrene. Some examples of vinyl aromatic monomers that can be utilized include styrene, 1-vinylnaphthalene, 2-vinylnaphthalene, α-methylstyrene, 4-phenylstyrene, 3-methylstyrene, t-butylstyrene, and the like.

The polymer may be synthesized by emulsion polymerization, solution polymerization, vapor phase polymerization or bulk polymerization. The polymerization process can be conducted as a batch, semi-continuous, or continuous process. Examples of useful rubber material include butyl rubber, epichlorohydrin rubber, natural rubber, isoprene rubber, chloroprene rubber, styrene rubber, nitrile rubber, ethylene-propylene rubber, ethylene-propylene-diene rubber, butadiene rubber, styrene-butadiene rubber, acrylic rubber, urethane rubber, fluoro rubber and silicone rubber, among others.

In specific embodiments, imidazolium treated clays such as micas may be loaded in a brominated polymer derived from a copolymer of isobutylene and p-methylstyrene (Exxpro), butyl rubber, Br-IIR, or a resin such as nylon, PP, PET, etc.

The present invention provides a process for making an article such as a tire comprising the steps of (1) kneading (a) a polymer; (b) a nano-composite as described above; and (c) conventional rubber compounding ingredients to produce a mixture; (2) forming an article from the mixture; and (3) vulcanizing the article.

Conventional rubber compounding ingredients include curing agents, cure accelerators, cure activators, curing aids such as sulfur, processing aids, conventional fillers, fatty acid, zinc oxide, waxes, reinforcing agents, oils, cure retarders, resins including tackifying resins, peptizing agents, extenders, stabilizers, plasticizers, antidegradants, antioxidants, antiozonants, pigments, fragrances, and the mixture thereof.

Specific examples of useful antioxidants and stabilizers include 2-(2'-hydroxy-5'-methylphenyl) benzotriazole, nickel di-butyl-di-thiocarbamate, tris(nonylphenyl) phosphite, 2,6-di-t-butyl-4-methylphenol, and the like. Other representative antioxidants may be, for example, diphenyl-p-phenylenediamine and those disclosed in *The Vanderbilt Rubber Handbook* (1978), Pages 344 through 346.

Exemplary fillers and pigments include silica, carbon black, titanium dioxide, iron oxide, and the like. In some embodiments, it will be beneficial to utilize a combination of silica and carbon black as the filler. It is to be appreciated that the silica coupler may be used in conjunction with a carbon black (namely, pre-mixed with a carbon black prior to addition to the composition). Talc can also be included as a portion of the filler to reduce cost.

Suitable reinforcing materials are inorganic or organic products of high molecular weight. Examples include glass fibers, asbestos, boron fibers, carbon and graphite fibers, whiskers, quartz and silica fibers, ceramic fibers, metal fibers, natural organic fibers, and synthetic organic fibers. Suitable processing aids can include, for example, aromatic, napthenic, and/or paraffinic processing oils. Suitable types of accelerators that may be used in the present invention are amines, disulfides, guanidines, thioureas, thiazoles, thiurams, sulfenamides, dithiocarbamates and xanthates.

The kneading may be conducted in a bulk thermomechanical mixer at a temperature within the range of from about 25° C. to about 250° C., preferably from about 50° C. to about 200° C., more preferably from about 70° C. to about 180° C.

In exemplary embodiments, the nano-composite can be incorporated into a polymer such as butyl rubber by any method known to a skilled artisan, for example, wet/solvent method or a dry mixing method under mild mixing conditions. Such mild mixing conditions are similar to those normally used in butyl rubber mixing. The mixing may be accomplished, for example, by using any integral mixing device such as a Brabender mixer, a twinscrew extruder or a kneader, at a mixing rate of from about 20 to about 200 rpm, at a temperature of about 25° C. to about 250° C. for a period of about 3~30 minutes. The mixing conditions for example include mixing in a Brabender mixer at about 60 rpm at a temperature of about 70° C. for about three minutes.

In exemplary embodiments, the vulcanization is conducted in the presence of a sulfur-vulcanizing agent. Examples of suitable sulfur vulcanizing agents include elemental sulfur (free sulfur) or sulfur donating vulcanizing agents, for example, an amine disulfide, polymeric polysulfide or sulfur olefin adducts. Preferably, the sulfur-vulcanizing agent is elemental sulfur.

Tires made in accord with this invention can be cured over a wide temperature range. However, curing at a temperature ranging from about 100° C. to about 250° C. may be preferred. It is generally preferred for the cure cycle used to vulcanize the tire to have a duration of about 5 minutes to about 60 minutes with a cure cycle of about 10 minutes to about 40 minutes being preferred.

The technology developed in the present invention can be used to develop rubber compounds for tire inner liners, sidewall, tread rubber, hose and containers.

A butyl rubber composition of this invention is useful in applications requiring good damping characteristics, such as engine mounts. Other uses include air cushions, pneumatic springs, air bellows, accumulator bags, tire-curing bladders, high temperature service hoses, and conveyor belts for handling hot materials.

The following examples are included to provide additional guidance to those skilled in the art in practicing the claimed invention. The examples provided are merely representative of the work that contributes to the teaching of the present application. Accordingly, these examples are not intended to limit the invention, as defined in the appended claims.

EXAMPLES

Preparation of Organo-Mica

Example 1

56 g of the 1,3-dibenzyl-2-methyl imidazolium chloride (Shikoku Chemicals Corp. DB2MZ-Cl), 100 g of ME100 (Coop Chemical, Co.) and 3000 g of deionized water were mixed together in a bottle and tumbled overnight. The solution was filtered and the treated mica was collected. Then, about 400 g of the treated mica containing water and 2000 g of isopropanol were mixed together and tumbled for 4 hours. Then the solution was filtered and the treated mica was collected. After that, it was dried in vacuum. TGA analysis showed that the treated mica contained 83.34% of the inorganic residue.

Reference 1

Sample 1: the synthesis of 1-benzyl-3-hexadecanyl imidazolium chloride 103 g of 1-benzylimidazole (Aldrich) and 170 g of 1-chlorohexadecane (Aldrich) were added into a 2000 ml three-neck round-bottom flask. A refluxing/cooling condenser was set on the left neck. A thermometer was set on the right neck. A rubber stopper was set on the middle neck. Nitrogen gas was breathed into the liquid phase through the needle from the middle neck. The reactants were mixed with vigorous stirring using a magnetic stirrer. Temperature was kept between 70 and 80° C. After heating up, 1-benzyl imidazole dissolved into 1-chlorohexadecane. The solution in the flask turned into red brown solution. The reaction was continued for three days. Then, the product was cooled down. The white product came out the solution. The product was washed with ethyl acetate five times. After that, it was dried in vacuum for seven hours at about 50° C.

100 g of the product from Sample 1, 50 g of ME100 (Coop Chemical, Co.) and 1000 g of deionized water were mixed together in a bottle and tumbled overnight. The solution was filtered and the treated mica was collected. Then, about 240 g of the treated mica containing water and 2000 g of isopropanol were mixed together and tumbled for 4 hours. Then the solution was filtered and the treated mica was collected. After that, it was dried in vacuum. TGA analysis showed that the treated mica contained 67.13% of the inorganic residue.

Reference 2

MAE was purchased from Coop Chemicals, Co. MAE represented that ME100 was treated with dimetyl ditallow ammonium.

TGA analysis results for Example 1, Reference 1, and Reference 2 are shown in FIG. 4.

Example 2 Brabender Method 25.9 g of 1-benzyl-2-methyl imidazole (Shikoku Chemicals Co. 1 B2MZ) and 19.0 g of benzyl chloride were put in 65 g brabender at room temperature under nitrogen atmosphere. Temperature was set at 90° C. However, the mixing torque did not increase. Then, temperature was set at 140° C. After 15 mins., a white product appeared. Temperature was set at 220° C. to react 1-benzyl-2-methyl imidazole with benzyl chloride completely. After one hour mixing, product was cooled down below room temperature. Finally a yellow product was obtained.

Example 3 (Purification)

Example 2 was washed with hexane four times. Then it was dried in vacuum for seven hours at about 50° C.

Reference 3

492.3 g of 1-benzyl-2-methyl imidazole (Shikoku Chemicals Co. IB2MZ) and 371.7 g of benzyl chloride were added into a 2000 ml three-neck round-bottom flask. A refluxing/cooling condenser was set on the left neck. A thermometer was set on the right neck. A rubber stopper was set on the middle neck. Nitrogen gas was breathed into the liquid phase through the needle from the middle neck. The reactants were mixed with vigorous stirring using a magnetic stirrer. The solution in the flask turned into yellow solution. Then, temperature was kept at 100° C. The reaction was continued for one day. The white yellow solid product appeared. Then, the product was cooled down. 300 ml of dried THF was added. The reaction was continued for three days at 70° C. The product was cooled down. Isopropanol was added. The product was dissolved into isopropanol. After the solution was transferred to 1 gallon jar, isopropanol was removed with nitrogen bubbling. The product was washed with hexane seven times. After that, it was dried in vacuum for seven hours at about 50° C.

The products were identified with NMR. The purity of the products from NMR and melting point from DSC were summarized at Table 1.

TABLE 1

| | Purity | Melting point (° C.) |
|---|---|---|
| DB2MZ-Cl | 99% | 216.79 |
| Example 2 | 99% | 214.48 |
| Example 3 | 99% | 215.32 |
| Reference 3 | 90% | 210.80 |

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

The invention claimed is:

1. A method, comprising:
 (i) combining two or more reactants,
 (ii) mixing the reactants in the substantial absence of a solvent in a mixing apparatus,
 (iii) collecting the imidazolium surfactant, and
 (iv) adding the imidazolium surfactant to a clay, wherein the imidazolium surfactant comprises one of the following compounds:

(I-2)

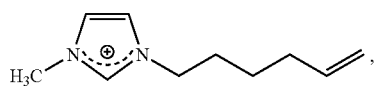
(I-3)

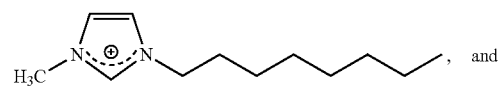
(I-9)

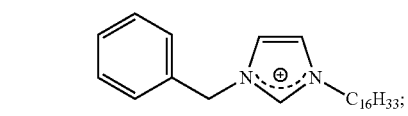
(I-10)

wherein the clay is a layered silicate clay and is intercalated with the surfactant.

2. The method according to claim 1, wherein the mixing apparatus is selected from the group consisting of a Brabender mixer, a Brabender plastograph, a two-stem mixer, a twin-screw extruder, a single-screw extruder, a plastomill or a rubber mill, a Banbury mixer, a Buss-Ko kneader, a Farrel continuous mixer, a Henschel mixer, a ribbon blender, a V-type blender, a mixing roll, a kneader, a static mixer, an impingement mixer, and combination thereof.

3. The method according to claim 1, wherein step (ii) is conducted for a time of about 15 minutes to about 90 minutes.

4. The method according to claim 1, wherein step (ii) is conducted at a temperature from about 23° C. to about 200° C.

5. The method according to claim 1, wherein the reactants comprise at least a halogenated $C_{\geq 6}$ hydrocarbon and an imidazole derivative.

6. A method comprising:
 (i) combining two or more reactants, the reactants comprising at least a halogenated $C_{\geq 3}$ hydrocarbon and an imidazole derivative;
 (ii) mixing the reactants in the substantial absence of a solvent in a mixing apparatus,
 (iii) collecting the imidazolium surfactant, and
 (iv) adding the imidazolium surfactant to a clay, wherein the imidazolium surfactant product has a general formula (I) as shown below:

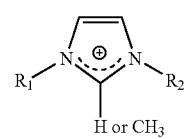
(I)

wherein at least one of $R_1$ and $R_2$ group comprises a cyclic alkyl or arylalkyl having from three to fifty carbon atoms;
wherein the clay is a layered silicate clay and is intercalated with the surfactant.

7. The method of claim 6, wherein the imidazolium surfactant product comprises one or more of the following compounds:

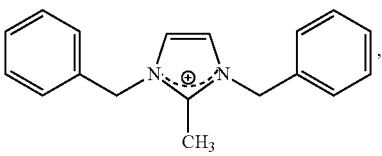
(I-1)

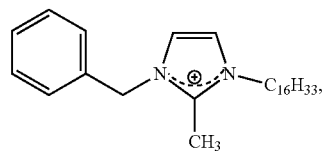
(I-4)

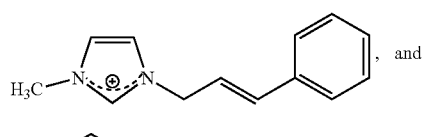
(I-5)

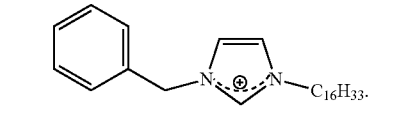
(I-10)

8. A layered silicate clay, wherein said clay comprises an imidazolium surfactant selected from the group consisting of:

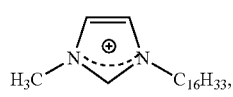
(I-2)

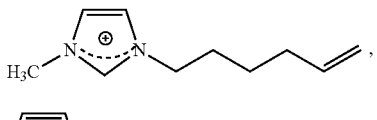
(I-3)

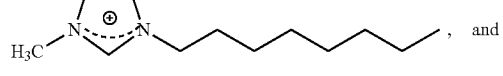
(I-9)

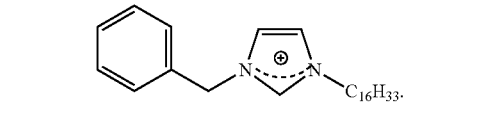
(I-10)

9. The clay according to claim 8, wherein the weight ratio between the clay and the imidazolium surfactant is from about 30:70 to about 70:30.

10. The clay according to claim 8, further comprising a surfactant selected from the group consisting of methyl tallow bis-2-hydroxyethyl ammonium salt, dimethyl hydrogenated-tallow (2-ethylhexyl) ammonium salt, dimethyl benzyl hydrogenated-tallow ammonium salt, dimethyl dihydrogenated tallow ammonium salt, N-tallow alkyltrimethylenediamine, hydrogenated tallow amine, octadecylamine, octadecylamine and γ-aminopropyltriethoxy silane, polyoxyethylene decycloxypropylamine, n-dodecylpyrrolidone, and the mixture thereof.

11. A clay, wherein said clay is intercalated with an imidazolium surfactant according to the formula:

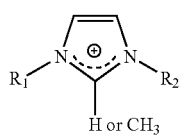
(I)

wherein at least one of $R_1$ and $R_2$ group comprises a cyclic alkyl or arylalkyl having from three to fifty carbon atoms.

12. A clay according to claim 11, wherein said imidazolium surfactant is selected from the group consisting of:

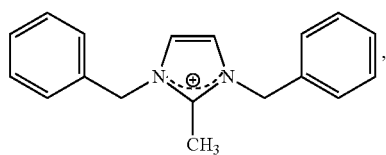
(I-1)

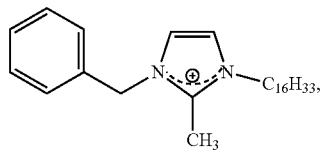
(I-4)

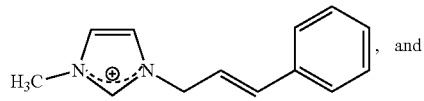
(I-5)

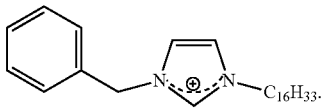
(I-10)

13. The clay according to claim 11, wherein the weight ratio between the clay and the imidazolium surfactant is from about 30:70 to about 70:30.

14. The clay according to claim 11, further comprising a surfactant selected from the group consisting of methyl tallow bis-2-hydroxyethyl ammonium salt, dimethyl hydrogenated-tallow (2-ethylhexyl) ammonium salt, dimethyl benzyl hydrogenated-tallow ammonium salt, dimethyl dihydrogenated tallow ammonium salt, N-tallow alkyltrimethylenediamine, hydrogenated tallow amine, octadecylamine, octadecylamine and γ-aminopropyltriethoxy silane, polyoxyethylene decycloxypropylamine, n-dodecylpyrrolidone, and the mixture thereof.

\* \* \* \* \*